United States Patent [19]

VanAntwerp et al.

[11] Patent Number: 5,433,710
[45] Date of Patent: Jul. 18, 1995

[54] MEDICATION INFUSION PUMP WITH FLUOROPOLYMER VALVE SEAT

[75] Inventors: William P. VanAntwerp, Los Angeles; Virote Indravudh, Saugus, both of Calif.

[73] Assignee: MiniMed, Inc., Sylmar, Calif.

[21] Appl. No.: 265,507

[22] Filed: Jun. 24, 1994

Related U.S. Application Data

[63] Continuation of Ser. No. 32,038, Mar. 16, 1993, abandoned.

[51] Int. Cl.6 ............................ A61M 1/00; F16L 5/00
[52] U.S. Cl. .................................. 604/152; 604/892.1; 137/359; 137/364
[58] Field of Search ................... 604/891.1, 892.1, 131, 604/151, 152, 9; 137/359, 364

[56] References Cited

U.S. PATENT DOCUMENTS

| | | | |
|---|---|---|---|
| 2,402,950 | 7/1946 | Culver et al. | 251/359 |
| 2,519,541 | 8/1950 | Bryant | 251/359 |
| 4,034,959 | 12/1977 | Morrison | 251/364 |
| 4,163,544 | 8/1979 | Fowler et al. | 251/364 |
| 4,560,375 | 12/1985 | Schulte et al. | 604/9 |
| 4,568,250 | 2/1986 | Falk et al. | 417/254 |
| 4,573,994 | 3/1986 | Fischell et al. | 604/891.1 |
| 4,958,661 | 9/1990 | Holtermann | 137/843 |
| 5,178,366 | 1/1993 | Kojima et al. | 251/359 |

Primary Examiner—John G. Weiss
Attorney, Agent, or Firm—Kelly Bauersfeld & Lowry

[57] ABSTRACT

A medication infusion pump is provided for use in the programmable delivery of a selected medication to a patient, wherein the pump includes a fluoropolymer valve seat engageable with a nonmetallic valve member. The fluoropolymer valve seat defines a substantially inert and nonadherent surface to prevent accumulation of medication deposits thereon. Such deposits are believed to occur as a result of shear denaturation and/or precipitation in the vicinity of the valve seat, in response to relatively high compression forces applied to the medication as the valve member opens and closes. The fluoropolymer valve seat provides a surface which is particularly nonadherent to protein based medications, such as insulin.

21 Claims, 2 Drawing Sheets

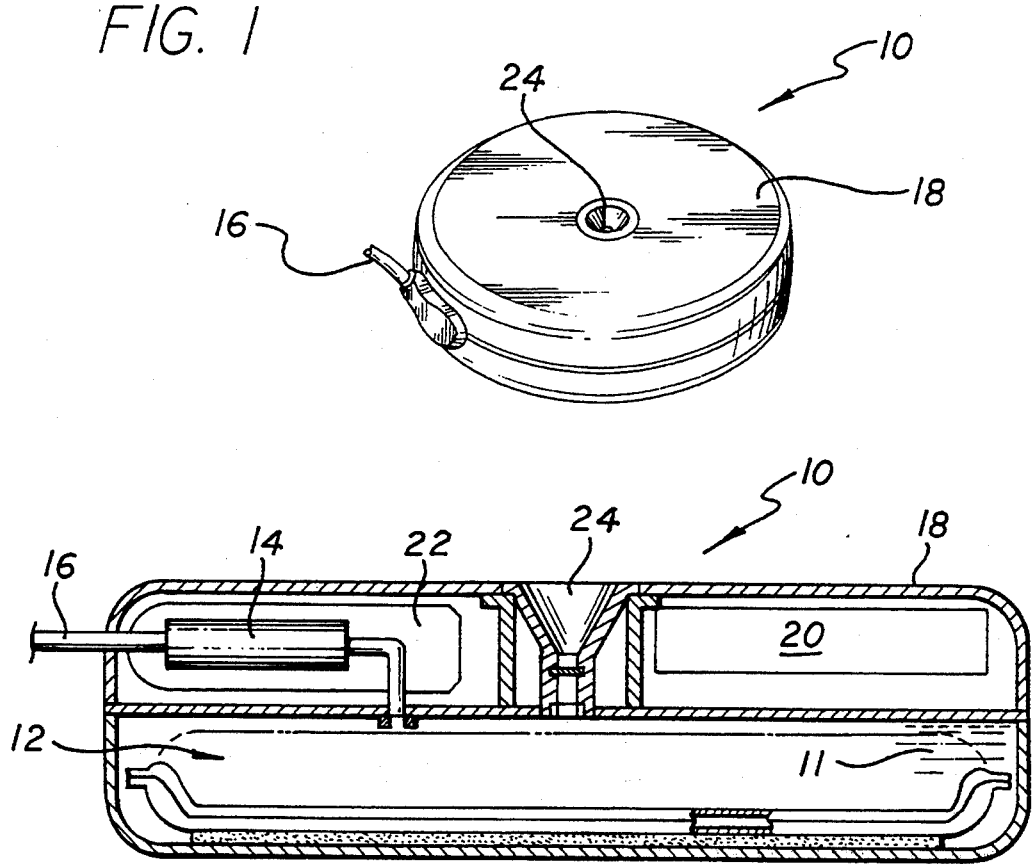
FIG. 1
FIG. 2
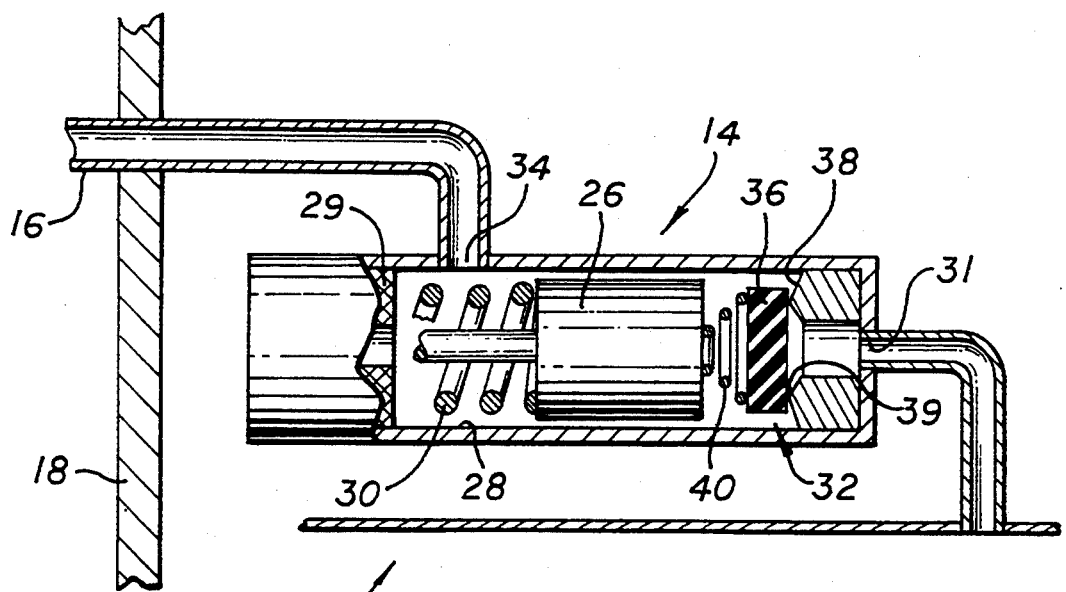
FIG. 3

MEDICATION INFUSION PUMP WITH FLUOROPOLYMER VALVE SEAT

This application is a continuation of application Ser. No. 08/032,038, filed Mar. 16, 1993, now abandoned.

BACKGROUND OF THE INVENTION

FIELD OF THE INVENTION

The present invention relates generally to medication infusion pumps, particularly of the type adapted for implantation directly into the body of a patient and for programmed operation to deliver medication to the patient, and more particularly to a medication infusion pump having an improved valve seat designed to minimize or prevent accumulation of medication deposits thereon.

Medication infusion pumps are generally known in the art for use in delivering a selected medication to a patient in a scheduled or preprogrammed manner. In recent years, infusion pumps have been developed in compact form and adapted for direct implantation into the body of a patient, to deliver a specific medication such as insulin to the patient in discrete doses over an extended time period. An implantable infusion pump of this general type includes an internal medication chamber for receiving and storing a supply of the selected medication in liquid form, in combination with a miniature pump mechanism and associated programmable control means for operating the pump mechanism to deliver discrete doses of the medication from the internal storage chamber and through a catheter to the patient. For one illustrative example of an implantable medication infusion pump of this general type, see U.S. Pat. No. 4,573,994, to Fischell et al.

The internal pump mechanism typically comprises an electromagnetically driven pulsatile pump having a solenoid operated piston mounted for reciprocation within a cylinder to draw medication from the internal storage chamber, and to deliver such medication through the catheter to the patient. The pulsatile piston operates in conjunction with an inlet check valve having a spring-loaded valve member movable between open and closed positions with respect to an annular valve seat. The valve member and valve seat are normally constructed from biocompatable and relatively inert materials, such as a movable valve disk of a silicone elastomer material and a rigid annular valve seat defined at the end of a ferrule formed of a titanium or titanium alloy. For examples of pulsatile pump mechanisms used in implantable infusion pumps, see U.S. Pat. No. 4,568,250, to Falk et al.; U.S. Pat. No. 4,569,641, to Falk et al.; U.S. Pat. No. 4,636,150, to Falk et al.; and U.S. Pat. No. 4,714,234, to Falk et al.

Despite the relatively inert characteristics of the traditional valve member and valve seat materials, medication deposits having a particle-like structure are known to accumulate over a period of time in the vicinity of the valve seat. The formation of such medication deposits is believed to be attributable to shear denaturation and/or precipitation of pharmaceutical components in response to relatively high mechanical stresses applied to the medication in the immediate vicinity of the valve seat, as the valve member moves between the open and closed positions. Such deposits are especially likely when relatively complex medications having a relatively large molecular structure are used, such as protein based pharmaceuticals including insulin and others.

Moreover, protein and other organic constituents present in such pharmaceuticals exhibit a tendency to adhere to the surface of titanium metal components, resulting in an accumulation of proteinaceous deposits at the valve seat. This presence of medication deposits is undesirable and may over time result in valve leakage, typically in the form of undesirable back-flow of body fluids into the interior of the implanted infusion pump.

There exists, therefore, a need for improvements in pump mechanisms for use in medication infusion pumps, wherein the pump mechanism includes an internal check valve designed to minimize or eliminate accumulation of medication deposits in the vicinity of a valve seat. It is accordingly the objective of the present invention to fulfill these needs and to provide further related advantages.

SUMMARY OF THE INVENTION

The disadvantages and limitations of the background art discussed above are overcome by the present invention. With this invention, a medication infusion pump is provided for programmable delivery of a selected medication to a patient, wherein the infusion pump includes an internal pump mechanism having a check valve defining substantially inert and nonadherent surfaces to prevent accumulation of medication deposits thereon. The check valve comprises a valve member and an associated valve seat which define nonmetallic and substantially nonadherent surfaces to prevent sticking and accumulation of medication deposits in the vicinity of the valve seat.

In the preferred form, the valve member comprises a movable disk of a silicone elastomer material or the like for opening and closure movement relative to an annular valve seat. The valve seat is defined by a fluoropolymer material to provide a substantially inert and highly nonadherent surface. In the preferred embodiment, the valve seat consists of a one-piece annular element made of fluoropolymer material. In another preferred form, the fluoropolymer valve seat is formed by a fluoropolymer cap mounted onto a ferrule base of titanium or titanium alloy. In still another preferred form, a ferrule base includes a fluoropolymer coating applied thereto to define the valve seat surface. In yet another form, a ferrule base includes an annular groove for seated reception of a fluoropolymer ring in a position defining the valve seat for closure engagement with the valve member.

Other features and advantages of the present invention will become more apparent from the following detailed description taken in conjunction with the accompanying drawings, which together illustrate, by way of example, the principles of the invention.

DESCRIPTION OF THE DRAWINGS

These and other advantages of the present invention are best understood with reference to the drawings, in which:

FIG. 1 is a perspective view depicting a typical implantable medication infusion pump;

FIG. 2 is an enlarged and somewhat schematic vertical sectional view of the pump of FIG. 1, and illustrating an internal pump mechanism for delivering medication from a storage reservoir to a patient;

FIG. 3 is an enlarged and somewhat schematic sectional view illustrating portions of an internal pump mechanism, constructed to include a one-piece fluoropolymer valve seat member in accordance with the preferred embodiment and illustrating the novel features of the invention;

DETAILED DESCRIPTION OF THE PREFERRED EMBODIMENT

Figure 4:
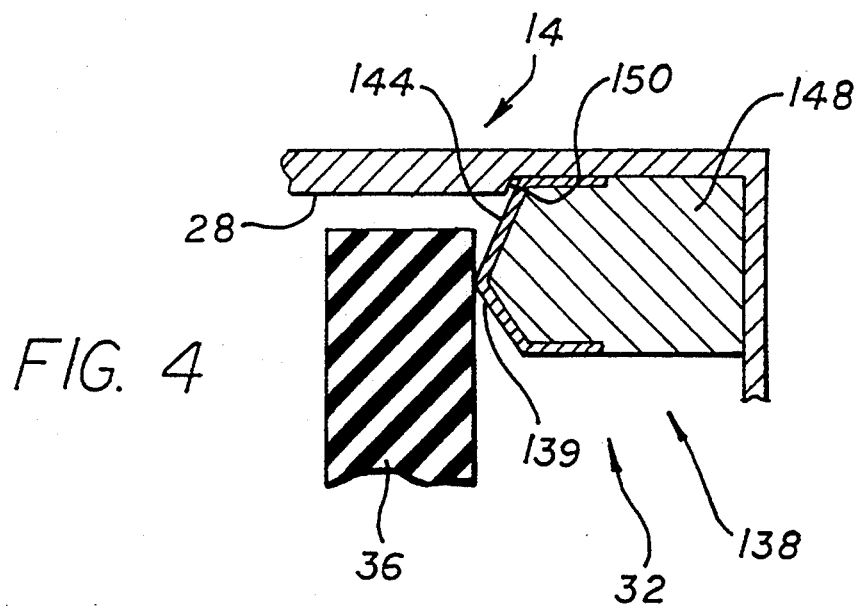
FIG. 4 is an enlarged fragmented sectional view corresponding with a portion of the valve seat depicted in FIG. 3, and illustrating another alternative preferred form of the invention.

As shown in the exemplary drawings, an implantable medication infusion pump referred to generally in FIGS. 1 and 2 by the reference numeral 10 is provided for use in administering a selected medication to a patient in a controlled, preprogramed manner. The infusion pump 10 receives and stores a quantity of the selected medication 11 within an internal medication chamber 12 (FIG. 2). The internal medication chamber 12 may be of the type shown in FIG. 2, or it may also be a flexible metal bellows reservoir as shown in U.S. Pat. No. 4,573,994, to Fischell et al.

A miniature pump mechanism 14 is provided for delivering the medication from the chamber 12 through a catheter 16 to the patient. In accordance with the invention, the pump mechanism 14 includes a check valve (not shown in FIGS. 1 and 2) having substantially inert and highly nonadherent valve surfaces to prevent accumulation of medication deposits and resultant potential for valve leakage.

The illustrative medication infusion pump 10 comprises a small substantially self-contained unit adapted for direct implantation into the body of patient. The pump 10 comprises an hermetically sealed pump housing or case 18 formed from a biocompatable material, such as titanium or a titanium alloy. The pump housing 18 defines the internal medication chamber 12 for receiving and storing the supply of the selected medication 11 in liquid form, such as insulin for a diabetic patient. The pump housing 18 encases the internal pump mechanism 14 in combination with electronic control circuitry 20 and a battery 22 for periodically operating the pump 14 to deliver medication doses via the catheter 16 to the patient. The control circuitry 20 is suitably preprogrammed to deliver the medication in accordance with individual patient need.

An inlet or refill fitting 24 on the pump housing 18 is adapted to receive a hypodermic needle (not shown) to permit percutaneous refilling of the medication chamber 12 without requiring surgical access to the infusion pump 10. For a more detailed description of the overall construction and operation of implantable infusion pumps of this general type, see U.S. Pat. No. 4,373,527, to Fischell; and U.S. Pat. No. 4,573,994, to Fischell et al., both of which are hereby incorporated herein by reference.

As shown generally in FIG. 3, the internal pump mechanism 14 comprises a positive displacement, solenoid operated pulsatile pump device having a piston 26 adapted for reciprocal displacement within a pump cylinder 28. In this regard, the piston 26 is drawn electromagnetically by a coil 29 in a first direction followed by a return stroke in an opposite, second direction under the influence of a return spring 30. With this reciprocal action, the piston 26 functions to draw the medication into the pump cylinder 28 via an inflow port 31, past an inlet check valve 32 into the cylinder 28, followed by delivery of the medication from the pump cylinder and through an outflow port 34 and via the catheter 16 to the patient.

The check valve 32 comprises a valve member 36 shown in the form of a resilient valve disk movably carried at one end of the piston 26 for engaging a one-piece annular valve seat 38 which circumscribes the inflow port 31. A biasing spring 40 is interposed between the piston 26 and the valve disk 36 for spring-loading the valve disk toward a closed position seated upon the annular valve seat 38, as the piston 26 strokes toward the annular valve seat 38. Further details of the overall construction and operation of the pump mechanism 14 may be found by reference to U.S. Pat. No. 4,568,250, to Falk et al.; U.S. Pat. No. 4,569,241, to Falk et al.; U.S. Pat. No. 4,636,150, to Falk et al.; and U.S. Pat. No. 4,714,234, to Falk et al., all of which are hereby incorporated herein by reference.

FIG. 3 illustrates the preferred configuration for the interengaging surfaces of the valve disk 36 and the annular valve seat 38 in accordance with the present invention. More particularly, as shown, the annular valve seat 38 comprises a one-piece, rigid annular structure defining a relatively narrow or discrete circular edge 39 presented axially in a direction toward the adjacent valve disk 36. The valve disk 36 is formed from a resilient elastomer material, such as silicone rubber, for resilient and conforming engagement with the valve seat. Over a period of time, a portion of the valve disk 36 may assume a recessed geometric set in approximate conformance with the shape of the circular edge 39 of the annular valve seat 38.

As the piston 26 is driven reciprocally within the pump cylinder 28, the valve disk 36 is displaced back and forth with respect to the annular valve seat 38, between open and closed positions. When the valve disk is in close proximity to the valve seat 38, upon opening or closure movement, the biasing force applied by the spring 40 is concentrated upon the narrow area of the valve seat edge 39, to result in a substantial mechanical compression force applied to a film of the medication then-present within the space between the valve disk 36 and the annular valve seat 38.

This substantial force can, by shear denaturation and/or precipitation, disrupt and break chemical bonds in a complex large molecule medication such as insulin, and thereby generate particle-like deposits in the vicinity of the valve seat. These deposits, consisting largely of protein and other organic constituents, exhibit a particular tendency to cling or adhere to titanium valve surfaces. Sufficient build-up of such deposits over a period of time can interfere with full closure of the check valve 32, and correspondingly result in undesirable back-flow leakage of body fluids from the patient into the medication chamber 12.

In accordance with the present invention, the surface of the annular valve seat 38, including the region of engagement with the valve member 36, is defined by a substantially inert, and substantially nonadherent material formed preferably from a selected fluoropolymer such as polytetrafluoroethylene, such as the material marketed by DuPont under the trademark TEFLON.

Alternative materials could also be used for the annular valve seat 38. Alternative materials include copolymers such as tetrafluoroethylene (such as the material marketed by DuPont under the trademark TEFZEL or by Dow under the trademark HALAR), chloropolymers such as polytetrachloroethylene, chlorofluoropolymers such as polychlorotrifluoroethylene (such as the material marketed by 3M under the trademark KEL-F), fluorosilicone acrylate, ultra-high molecular weight polyethylene or polypropylene, or fluoroepoxies. The desired characteristics of the material of the annular valve seat 38 are low surface energy plus a high degree of machinability. It will be understood that both the preferred embodiment and any of the alternate embodiments can utilize any of these materials.

A first alternate embodiment is shown in FIG. 4. An annular valve seat 138 comprises an annular cap 144 of polytetrafluoroethylene-based material which can be formed to close tolerance requirements to define the valve seat edge 139 with precision geometry. The preferred construction for the polytetrafluoroethylene cap 144 includes an underside surface shaped for substantially mated press-fit mounting onto a conforming surface on a ferrule base 148 of titanium or a titanium alloy.

If desired, a step 150 may be formed in the periphery of the cylinder 28 to assist in retaining the polytetrafluoroethylene cap 144 seated firmly upon the ferrule base 148. Importantly, with this geometry, the annular outwardly presented surface of the cap 144 defines the valve seat edge 139, having a substantially inert, low surface energy to avoid significant chemical interaction with the medication 11, and further to prevent and eliminate adherence of any particle-deposits which might be produced upon flow of the medication between the inlet valve disk and valve seat.

Figure 5:
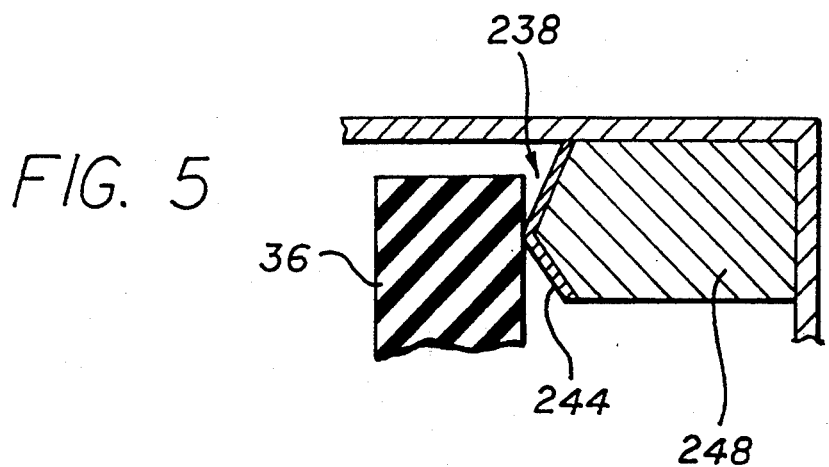
FIG. 5 is a enlarged fragmented sectional view similar to FIG. 4, and illustrating still another alternative preferred form of the invention.
Figure 6:
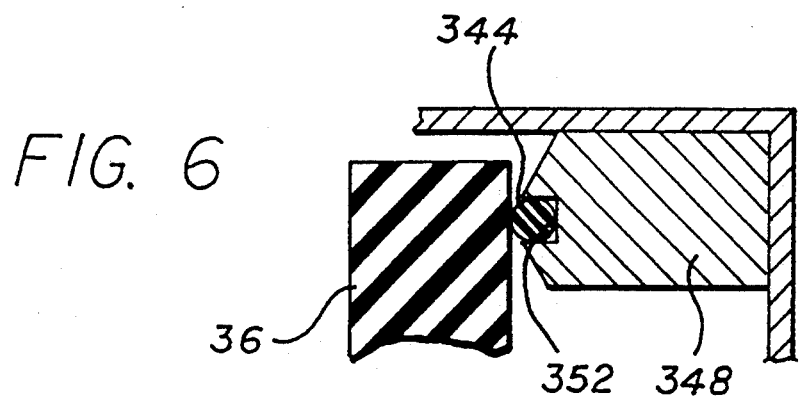
FIG. 6 is an enlarged fragmented sectional view similar to FIGS. 4 and 5, and illustrating still another alternative preferred embodiment of the invention.

FIGS. 5 and 6 illustrate additional alternative preferred forms of the invention. More specifically, with reference to FIG. 5, a ferrule base 248 of titanium or titanium alloy may be treated to include a surface coating 244 in the vicinity of an annular valve seat 238, thereby providing the desired valve seat surface of substantially inert and nonadherent material. FIG. 6 illustrates a ferrule base 348 having an annular groove 352 formed therein for seated, press-fit reception of a polytetrafluoroethylene ring 344. While a ring 344 of circular cross-section is shown, it will be understood that alternative ring configurations adapted for sealing engagement with the adjacent valve disk 36 may be used.

The present invention thus provides an improved valve device for a pump mechanism employed within a medication infusion pump 10, wherein the valve device is constructed with nonmetallic and substantially nonadherent valve surfaces to minimize and/or eliminate accumulation of medication deposits at the valve seat. The preferred valve construction includes a fluoropolymer valve seat surface in combination with a nonmetallic valve member of a silicone elastomer or the like.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. For example, it will be understood that the fluoropolymer valve seat and silicone elastomer valve disk materials may be reversed. All such changes, modifications, and alterations should therefore be seen as being within the scope of the present invention.

What is claimed is:

1. A medication infusion pump, comprising:
    a housing defining a medication chamber for receiving and storing a supply of a selected medication; and
    a pump mechanism for delivering the selected medication in a controlled manner from said medication chamber to a patient, said pump mechanism including a valve having a valve member movable between open and closed positions relative to a valve seat, and spring means for applying a biasing force to said valve member to normally retain said valve member against said valve seat in said closed position, said valve member and said valve seat being formed from nonmetallic and substantially inert materials defining substantially nonadherent surfaces in the vicinity of said valve seat to prevent accumulation of medication deposits on said valve seat.

2. A medication infusion pump as defined in claim 1, wherein said valve member is formed from an elastomer material, and wherein said valve seat includes a valve seat surface formed from a material from the group consisting of fluoropolymer materials, chloropolymer materials, chlorofluoropolymer materials, copolymers, fluorosilicone acrylate, fluoroepoxy materials, and ultra-high molecular weight polyethylenes or polypropylenes.

3. A medication infusion pump as defined in claim 2, wherein said valve member is formed from a silicone elastomer.

4. A medication infusion pump as defined in claim 2, wherein said valve seat comprises a ferrule base having a fluoropolymer cap mounted thereon, said cap defining said valve seat surface.

5. A medication infusion pump as defined in claim 4, wherein said cap is press-fit mounted onto said ferrule base.

6. A medication infusion pump as defined in claim 4, wherein said cap comprises a coating applied to said ferrule base.

7. A medication infusion pump as defined in claim 4, wherein said ferrule base has an annular groove formed therein, said cap comprising an annular ring seated within said groove.

8. A medication infusion pump as defined in claim 4, wherein said ferrule base is formed from a titanium material.

9. A medication infusion pump as defined in claim 4, including means for retaining said cap on said ferrule base.

10. In a medication infusion pump for delivering a selected medication in a controlled manner to a patient, a valve comprising:
    a valve member and a valve seat adapted for relative movement between a closed position with said valve member engaging said valve seat and an open position with said valve member spaced from said valve seat to permit flow of medication through said valve seat; and
    spring means for applying a biasing force to normally retain said valve member in engagement with said valve seat;
    said valve member and said valve seat having engageable surfaces formed from nonmetallic and substantially inert materials which are substantially nonadherent to medication deposits.

11. An infusion pump valve as defined in claim 10, wherein said valve member is formed from an elastomer material, and wherein said valve seat includes a valve seat surface formed from a material from the group consisting of fluoropolymer materials, chloropolymer materials, chlorofluoropolymer materials, copolymers, fluorosilicone acrylate, fluoroepoxy materials, and ultra-high molecular weight polyethylenes or polypropylenes.

12. An infusion pump valve as defined in claim 11, wherein said valve seat comprises a ferrule base having a fluoropolymer cap mounted thereon, said cap defining said valve seat surface.

13. An infusion pump valve as defined in claim 12, wherein said cap is press-fit mounted onto said ferrule base.

14. An infusion pump valve as defined in claim 12, wherein said cap comprises a coating applied to said ferrule base.

15. An infusion pump valve as defined in claim 12, wherein said ferrule base has an annular groove formed therein, said cap comprising an annular ring seated within said groove.

16. In a medication infusion pump for delivering a selected medication in a controlled manner to a patient, a valve comprising:
 a valve member formed from a substantially inert resilient elastomer;
 a valve seat defining an annular valve seat surface formed from a substantially inert and nonadherent material from the group consisting of fluoropolymer materials, chloropolymer materials, chlorofluoropolymer materials, copolymers, fluorosilicone acrylate, fluoroepoxy materials, and ultrahigh molecular weight polyethylenes or polypropylenes, said valve seat defining a medication flow port, and said valve member being movable relative to said valve seat between open and closed positions respectively spaced from and in engagement with said valve seat surface; and
 spring means for applying a biasing force to said valve member to normally retain said valve member in said closed position.

17. An infusion pump valve as defined in claim 16, wherein said valve seat comprises a ferrule base having a fluoropolymer cap mounted thereon, said cap defining said valve seat surface.

18. An infusion pump valve as defined in claim 17, wherein said cap is press-fit mounted onto said ferrule base.

19. An infusion pump valve as defined in claim 17, wherein said cap comprises a coating applied to said ferrule base.

20. A medication infusion pump as defined in claim 17, wherein said ferrule base has an annular groove formed therein, said cap comprising an annular ring seated within said groove.

21. A method of delivering a selected medication from a medication infusion pump in a controlled manner to a patient, said method comprising:
 storing a supply of a selected medication within a housing defining a medication chamber; and
 delivering the selected medication in a controlled manner from said medication chamber to a patient with a pump mechanism, said pump mechanism including a valve having a valve member and a valve seat adapted for relative movement between a closed position with said valve member engaging said valve seat and an open position with said valve member spaced from said valve seat to permit flow of medication through said valve seat, and spring means for applying a biasing force to said valve member for normally retaining said valve member in the closed position, said valve member and said valve seat having engagement surfaces which are formed from nonmetallic and substantially inert materials to prevent accumulation of medication deposits on said valve seat.

* * * * *